United States Patent [19]

Sterling et al.

[11] Patent Number: 5,753,228
[45] Date of Patent: May 19, 1998

[54] METHOD OF TREATING PARASITOSIS BY THE ENTERAL ADMINISTRATION OF HYPERIMMUNE HEN EGG YOLK ANTIBODIES

[75] Inventors: Charles R. Sterling; Vitaliano A. Cama, both of Tucson, Ariz.

[73] Assignee: Arizona Board of Regents on behalf of The University of Arizona, Tucson, Ariz.

[21] Appl. No.: 349,840

[22] Filed: Dec. 5, 1994

Related U.S. Application Data

[63] Continuation of Ser. No. 936,359, Aug. 25, 1992, abandoned.

[51] Int. Cl.$^6$ .................. A61K 39/395; C07K 16/00; C12P 21/08
[52] U.S. Cl. .................. 424/151.1; 424/130.1; 530/387.1; 530/388.6
[58] Field of Search .................. 424/130.1, 164.1, 424/177.1, 151.1; 530/387.1, 388.6, 389.1, 389.5

[56] References Cited

U.S. PATENT DOCUMENTS

| | | |
|---|---|---|
| 3,981,771 | 9/1976 | Sevolan . |
| 4,279,893 | 7/1981 | Kreimer et al. . |
| 4,324,782 | 4/1982 | Beck . |
| 4,357,272 | 11/1982 | Polson . |
| 4,477,432 | 10/1984 | Hardie . |
| 4,550,019 | 10/1985 | Polson . |
| 4,748,018 | 5/1988 | Stolle et al. . |
| 4,956,452 | 9/1990 | Snyder et al. . |
| 5,028,540 | 7/1991 | Humphries . |
| 5,049,502 | 9/1991 | Humphries . |
| 5,080,895 | 1/1992 | Tokoro . |

OTHER PUBLICATIONS

Jungling, A., et al. (1991) Chicken egg antibodies for prophylaxis and therapy of infection intestinal diseases. IV. In vitro studies on protective effects against adhesion . . . J. Vet. Med. B 38:373–381.

Kuhlmann, R., et al. (1988) Chicken egg antibodies for prophylaxis and therapy of infection intestinal diseases. I. Immunization and antibody determination. J. Vet. Med. B 35:610–616.

Schmidt, P., et al. (1989) Chicken egg antibodies for prophylaxis and therapy of infection intestinal diseases. II. In vitro studies on gastric and enteric digestion of egg yolk . . . J. Vet. Med. B 36:619–628.

Wiedemann, V., et al. (1989) Chicken egg antibodies for prophylaxis and therapy of infection intestinal diseases. III. In vivo tenacity test in piglets . . . J. Vet. Med. B 37:163–172.

Arrowood et al. 57: 2283–2288 (1989).

Kondo et al. Infection and Immunity 26: 19–24 (1979).

Winter et al. Infection and Immunity 42: 1159–1167 (1983).

Stedman's Medical Dictionary, 25th Ed., Henssyl, Editor, Williams & Wilkins, Publisher, (Jan. 1990).

Immunology, 2nd Ed., Roitt et al., Editor, Harper & Row, Publisher, (Jan. 1989).

Wiedemann et al., J. Vet. Med. Ser. B. 38:283–291, Apr. 1991.

Ungar et al., Gastroenterology. 98: 486–489, (Feb. 1990).

Tzipori et al., British Medical Journal. 293: 1276–1277, Nov. 1986.

Review of Medical Microbiology, 16th Ed., Jawetz et al., Editors, Lange, Publisher, Jan. 1984.

Akita, E., et al. Immunoglobulins from Egg Yolk: Isolation and Purification. J. Food Science 57:629–634 (1992).

Vieira, J., et al. Egg yolk as a source of antibiotic for human parathyroid hormone (hPTH) radioimmunoassay. J. Immunoassaay 121–129 (1984).

O'Farrelly, C., et al. Oral ingestion of egg yolk immunoglobulin from hens immunized with . . . Infection and Immunity 60:2593–2597 (1992).

Yokoyama, H., et al. Passive protective effect of chicken egg yolk immunoglobulins against . . . Infection and Immunity 60(3):998–1007 (1992).

Yolken, R., et al. Immunoglobulins and other modalities for the prevention and treatment of . . . J. Clin. Immunol. 10(6):80S–87S (1990).

Yolken, R., et al. Antibodies to rotaviruses in chickens' eggs: a potential source of antiviral . . . Pediatrics 81:291–295 (1988).

Yolken, R. Antibody to human rotavirus in cow's milk. New Engl. J. Med. 312:605–610 (1985).

Huang A., et al. Monoclonal antibody covalently coupled with fatty acid. J. Biol. Chem. 255:8015–8018 (1980).

Leslie, G., et al. Phylogeny of immunoglobulin structure and function. J. Exp. Med. 130:1337–1352 (1969).

Losch, U. The chicken egg, an antibody source. J. Vet. Med. B 33:609–619 (1986).

Marcial, M., et al. Cellular localization and structural analysis of absorptive cell–parasite . . . Gastroenterology 88:1489 (1985).

Otake, S., et al. Protection of rats against dental caries by passive immunization with . . . J. Dent. Res. 70(3):162–166 (1991).

Saxon, A., et al. Oral administration of bovine colostrum anti–cryptosporidia antibody fails . . . J. Parasitology 73(2):413–424 (1987).

(List continued on next page.)

*Primary Examiner*—Frank C. Eisenschenk
*Assistant Examiner*—Patrick Nolan
*Attorney, Agent, or Firm*—Knobbe Martens Olson & Bear LLP

[57] ABSTRACT

Egg yolks and egg yolk fractions containing effective therapeutic concentrations of avian antibodies against parasitic antigen, and a method of providing passive immunization for the prevention or treatment of intestinal parasitosis by enteral administration of egg yolk antibodies harvested from hyperimmunized avian hens. Also provided are pharmaceutical formulations comprising the egg yolk antibodies.

7 Claims, 1 Drawing Sheet

OTHER PUBLICATIONS

Alving, C.R. et al. Therapy of leishmaniasis: superior efficacies of . . . Proc. Natl. Acad. Sci. USA 75(6):2959–2963 (1978).

Bartz, C.R., et al. Prevention of murine rotavirus infection with chicken egg yolk . . . J. Infectious Dis. 142:439–441 (1980).

Bernhisel–Broadbent, J., et al. Allergenicity of orally administered immunoglobulin . . . Pediatrics 87:208–214 (1991).

Fayer, R., et al. Hyperimmune bovine colostrum neutralizes cryptosporidia sporozoites . . . J. Parasitol. 75:151–153 (1989).

Fayer, R., et al. Efficacy of hyperimmune bovine colostrum for prophylaxis of cryptosporidiosis in neonatal calves. J. Parasitol. 75:393–397 (1987).

Hamada S., et al. Oral Passive immunization against dental caries in rats by use of hen egg yolk . . . Infection and Immunity 59:4161–4167 (1991).

METHOD OF TREATING PARASITOSIS BY THE ENTERAL ADMINISTRATION OF HYPERIMMUNE HEN EGG YOLK ANTIBODIES

This application is a continuation of application Ser. No. 07/936,359, filed Aug. 25, 1992 now abandoned.

BACKGROUND OF THE INVENTION

The present invention relates to the passive transfer of immunity; it relates particularly to the passive transfer of immunity in vertebrates by means of egg yolk antibodies produced in hyperimmunized hens.

Passive immunization is an invaluable therapeutic strategy for providing immune protection to a patient in clinical situations in which it is impossible or impractical to develop an autologous immune response to either a threatened or existing infection. Examples of such patients are newborns that are not yet immunocompetent, as well as infants or adults that are immunocompromised by another disease, such as HIV infection, as a result of therapy in connection with organ transplants or as a result of malnutrition. Other examples are patients suffering from an infectious disease that cannot be controlled either by medications or through non-specific autologous immune mechanisms.

Passive immunization is carried out by transferring immune elements, usually IgG, from an immunized animal to the non-immune recipient. Passive immune transfer requires a reliable commercial supply of substantial amounts of high-titer immune globulin and entails the risk of sensitizing the recipient as a consequence of the parenteral administration of foreign protein. One new therapeutic approach that addresses these problems has been to immunize cows and collect hyperimmune bovine colostrum (HBC) in relatively large volume from the lactating animal. The colostrum, containing immune globulin, is then administered to a patient orally, thus avoiding sensitization to the foreign protein. An example of this approach is presented in U.S. Pat. No. 4,324,782 to Beck wherein dental caries is prevented in rats by administration to young animals, either by oral ingestion or application to the teeth, of bovine milk antibodies to *Streptococcus mutans*. The use of hyperimmune bovine colostrum in the large amounts required for passive immunization implies a continuous supply of HBC which is difficult to insure because of the natural interruptions in its production by lactating cows. Other difficulties in the production of HBC are the assurance of product uniformity, and healthful methods of collection and storage. Also, the processing of bovine milk products to make them suitable for consumption by newborns has been found to markedly reduce the concentration of antiviral antibodies (Yolken, R., *New Engl. J. Med.* 312:605–610 (1985)).

The use of antibodies from the egg yolks of hyperimmunized hens (HEY antibody) for immunological procedures and for passive transfers overcomes the limitations associated with the use of HBC antibodies, because it provides a continuous source of large quantities of uniform immunizing agent which can be easily collected and stored. The manufacture and collection of hen egg antibodies is well understood (U.S. Pat. Nos. 4,387,272 and 4,550,019 to Polson; and Losch, U., *Journal Veterinary Medicine B* 33:609–619 (1986)). Hen egg yolk antibodies thus produced have been used in a number of applications for passive transfer of immunity. U.S. Pat. No. 4,748,018 to Stolle, et al. discloses a method of passive immunization against bacterial infection comprising a preliminary development of tolerance to HEY by repeated oral ingestion of egg yolk, followed by parenteral injection of HEY antibody to a selected bacterial antigen. U.S. Pat. No. 5,080,895 to Tokoro discloses prevention of *E. coli* diarrhea in newborn piglets by oral administration of anti-bacterial hen egg yolk antibodies. Hamada, S., *Infection and Immunity* 59(11):4161–4167 (1991); and Otake, S., *J. Dental Research* 70(3):162–166 (1991) reproduced the results of Beck in protecting rats against dental caries by means of passive immunization with orally administered hen egg yolk antibodies against *S. mutans*. Bartz, C. et al., *J. Infectious Disease* 142(3):439–441 (1980) prevented murine rotaviral infection in mice by the oral administration of the water-soluble fraction of the eggs of immunized hens; Yokoyama, H., et al. *Infection and Immunity* 60(3):998–1007 (1992) succeeded in passively protecting neonatal piglets from fatal enterotoxigenic *E. coli* infection by oral administration of a crude yolk immunoglobulin fraction from the eggs of immunized hens. On the basis of animal studies, Yolken, R. et al., *Pediatrics* 81(2):291–295 (1988); and *Journal Clin. Immunol.* 10(6):80S–87S (1990), proposed the oral administration of antiviral HEY immunoglobulin for the prevention and treatment of enteric infections, including rotaviral infection in humans. Methods and formulations for the oral administration of immune globulin are known (U.S. Pat. No. 4,477,432 to Hardie). However, objections to this proposed form of therapy have been expressed based on the unfavorable sensitization reactions that could occur (Bernhisel-Broadbent, J. et al., *Pediatrics* 87(2):208–214 (1991)).

*Cryptosporidium parvum* (*C. parvum*) is a protozoan parasite that is endemic in calves and piglets, and occurs as well among young children in some countries. Gastrointestinal infection with the organism produces mild to severe diarrhea in immunologically healthy humans and animals, and can cause life threatening disease in immunocompromised individuals. It is considered one of the most important enteric opportunistic infections in AIDS patients. No therapeutic regimen has proved effective in humans, and treatment to date has been limited primarily to oral or parenteral rehydration. Experimental prophylaxis with hyperimmune bovine colostrum (HBC) prevented cryptosporidiosis in neonatal calves (Fayer, R. et al. *J. Parasitology* 75(3):393–397 (1989); and protected mice against a challenge with *C. parvum* oocysts (Fayer, R., *J. Parasitology* 75(1);153–157 (1989). Comparable compassionate therapy in humans, however, has had uncertain results. Ungar, B. et al., *Gastroenterology* 98:486–498 (1990), report the cessation of cryptosporidium-associated diarrhea and disappearance of oocysts in an AIDS patient after direct duodenal infusion treatment with hyperimmune bovine colostrum; however, the symptoms returned three months later. Tzipori, T., et al., *British Medical Journal* 293:1276–1277 (1986), report remission of vomiting and diarrhea, and disappearance of oocysts from the gut, in a hypogammaglobulinemic child with cryptosporidiosis, (and also infected with *Pneumocytis carinii*), after receiving hyperimmune bovine colostrum daily for about two weeks. Oocysts reappeared four months after cessation of treatment. Saxon, A. et al., *J. Parasitology* 73(2):415–417 (1987) administered bovine colostrum that was known to have antibody activity against oocysts and sporozoites of *C. parvum* to three patients having cryptosporidiosis (but without other enteric pathogens), two of whom had AIDS, and the third had congenital dysgammaglobulinemia type I (absent IgG). Treatment of these patients with quantities of 1 to 5 L/day of colostrum for a period of from 5 to 7 days was ineffective. Saxon concluded that the failure of oral antibody therapy for *C. parvum* occurred because the organisms enter the absorptive cells of the intestinal mucosa and wall themselves off intracellularly in an extracytoplasmic vesicle as described by Marcial and Madara, *Gastroenterology* 88:1489 (1985), where they are inaccessible to the antibodies of colostrum. Saxon notes that human breast milk is effective in preventing cryptosporidiosis in infants, and comments that the inconsistent results with HBC may occur because the IgG1 isotype of cow colostrum may not be as effective as the IgA antibodies in human breast milk, or alternatively, that antibodies of either type can only function as protective "preformed" immunity, that must be in place prior to infection; and, if that is the case, oral antibody therapy can only prevent, not cure, this infection. Finally, the infant gut does not exclude proteins, including immunoglobulins, as effectively as that of adults, indicating either therapy would be less useful for infected adults.

Accordingly, it is an object of the invention to develop useful procedures to apply the benefits of enteral immunotherapy to treat and prevent intestinal parasitic infections.

SUMMARY OF THE INVENTION

The invention provides hen egg yolks containing anti-parasite antibodies for therapeutic suitable for use against intestinal parasitic infections. In a preferred embodiment the hen egg yolk antibodies can have a specificity for protozoa, and in a particularly preferred embodiment, the hen egg yolk antibodies have a specificity for *C. parvum*. The hen egg yolk antibodies can have a specificity to an antigen of the oocyst, sporozoite, merozoite, or any sexual stage of the parasite. According to another embodiment of this aspect of the invention there is provided hen egg yolk antibodies to intestinal helminths.

The invention also provides a method of preventing or treating intestinal parasitosis in a vertebrate in need thereof, comprising the enteral administration of an effective parasite-reducing amount of anti-parasite hen egg yolk antibodies to said vertebrate. The enteral administration can comprise oral ingestion, delivery of the immunizing egg yolk antibodies by gastric intubation or through the rectum, or direct injection of the antibodies into the intestinal tract of said vertebrate. In a preferred embodiment of the invention, the vertebrate is infected with a parasitic protozoan. In a particularly preferred embodiment, the vertebrate is infected with *C. parvum*. The method can be used in cases wherein the vertebrate has an opportunistic infection, that occurs in cases wherein the vertebrate is immunologically compromised. An immunodeficiency that provides an opportunity for parasitic attack through the intestinal barrier can be caused by a genetic defect, as a result of infection, for example, by the HIV virus, or as a consequence of malnutrition, particularly in children.

According to the invention there is also provided a method of preparing avian egg yolks containing anti-parasite egg yolk antibodies, comprising the steps of stimulating an immune response in a hen fowl by parenteral administration of an immunogen prepared from a parasite; harvesting the eggs laid by the hen, and isolating anti-parasitic antibodies from the egg yolks. In a preferred embodiment of the method the parasite from which the immunogen is prepared is a protozoan intestinal parasite. In a particularly preferred embodiment, the immunogen is prepared from *C. parvum*. The immunogen can be prepared from oocysts, sporozoites, or the merozoites or from any of the sexual stages of the parasite. According to one aspect of this method of the invention, the immunogen is administered to the hens is combination with a responsiveness-enhancing amount of *Mycobacterium avian* as an adjuvant.

According to another embodiment of the invention there are provided hen egg yolks, or fractions thereof, containing anti-parasite antibodies prepared according to the above-described method of the invention. The egg yolk or yolk fractions can be cooked by heating to partially coagulate the yolk proteins. The invention also includes hen egg yolk antibodies prepared according to the method described.

According to another aspect of the invention there are provided pharmaceutical formulations for the prevention or therapy of a intestinal parasitosis in vertebrates, comprising an effective parasite-reducing concentration of an immunity-conferring immunoglobulin fraction, prepared from the eggs of a avian hen that has been hyperimmunized to an antigen of an intestinal parasite, in a pharmaceutically acceptable carrier. The immunity-conferring fraction comprises egg yolk antibodies. The antibodies can have a specificity to the agents of any parasitic infection that is introduced through the gut, and in preferred embodiment, comprises antibodies effective in the treatment of parasitic protozoan infections. In a particularly preferred embodiment, the intestinal parasite is *C. parvum*, and the egg preparation comprises HEY anti-*C. parvum* antibodies. In this embodiment, the avian egg yolk antibodies of the formulation can have a specificity to the oocysts, sporozoites, the merozoites, or any of the sexual stages of *C. parvum*. The invention also provides formulations wherein the anti-parasitic egg yolk antibodies are incorporated into a liposome, in which an anti-parasitic drug is also incorporated or encapsulated.

DETAILED DESCRIPTION OF THE INVENTION

Figure 1:
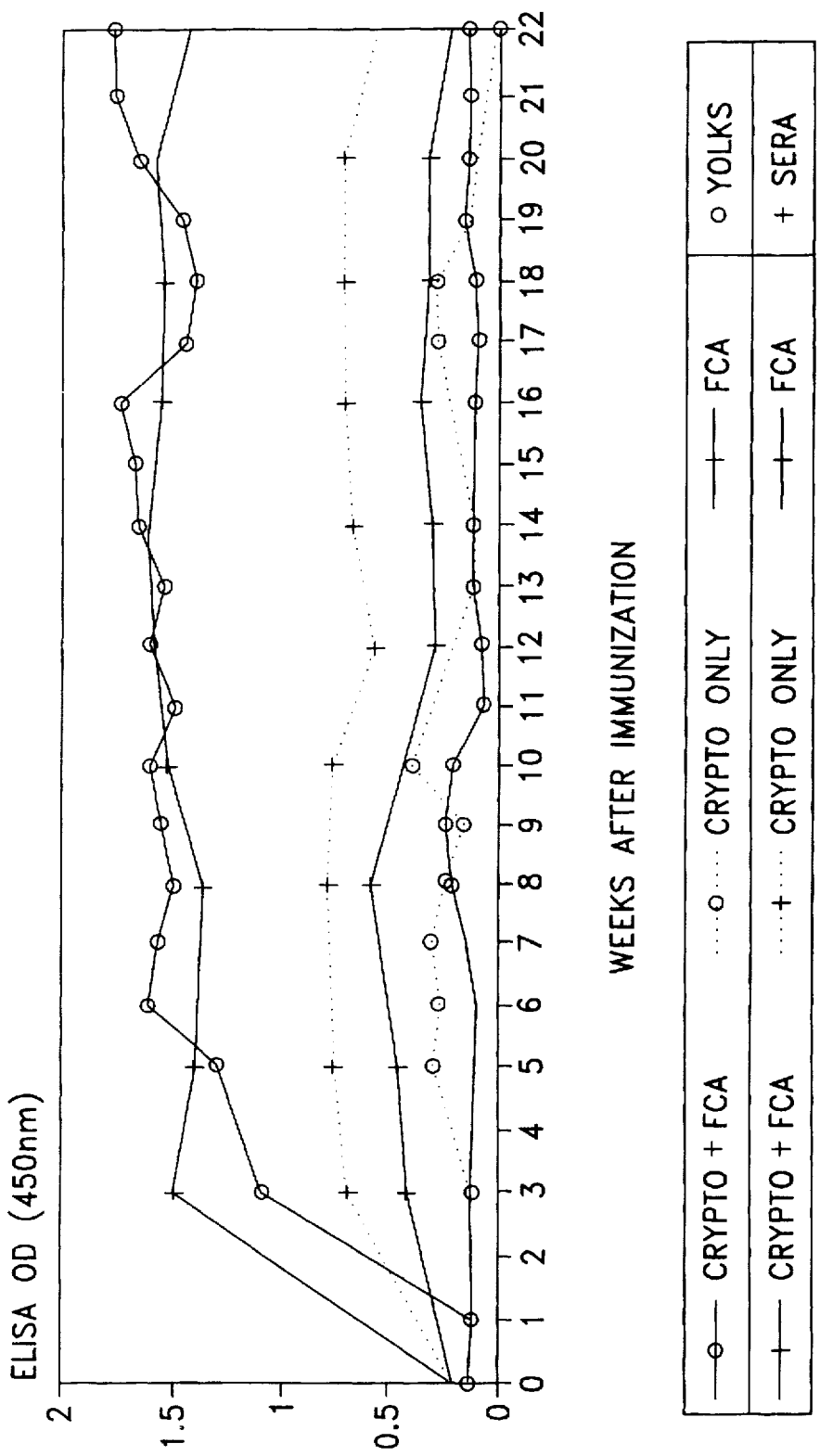
FIG. 1 demonstrates the levels of anti-*Cryptosporidium parvum* activities in the egg yolk and sera of hens following immunization.

Avian anti-parasite antibodies can be effectively used to prevent or to treat a parasitic infection in a vertebrate animal by the passive transfer of immunity when administered enterally. Egg yolks of avian hens hyperimmunized against a parasite antigen or group of such antigens, can provide an assured, continuous, sterile source of high-titer anti-parasitic antibodies in substantially unlimited volume. Enteral administration of the hen egg yolk antibody preparations can avoid problems of sensitization encountered with parenteral injection of foreign proteins into an animal, and also allows the universal administration of anti-parasitic antibody formulations to members of any species of animal in need of such prophylaxis or therapy.

Treatment according to the method of the invention is appropriate for any parasitic infection that is introduced through the gut. The parasitoses that are amenable to therapy by means of the method of the invention are those that enter through the digestive tract or by the intestinal route, and in a preferred embodiment, includes those due to protozoa, particularly those of *Isospora* spp., *Entamoeba histolytica*, *Giardia intestinalis*, and *Cyclopora cayentanensis*. *Toxoplasma gondii* infection is also amendable to treatment by this method. Further, the method of the invention can be applied, preferably as an adjunctive therapy, in the form of an antibody coupled to an anti-helminthic or anti-parasitic agent, to direct the agent to the site of parasitic helminth (worm) infestation.

In preferred embodiments, intestinal parasitoses are treated or prevented according to the methods of the invention, using hen egg yolk preparations containing the egg yolk anti-parasite antibodies of the invention. In a particularly preferred embodiment, *C. parvum* parasitosis in a vertebrate is treated by the oral administration of anti-*C. parvum* hen egg yolk antibodies.

Production of HEY Anti-parasite Antibodies

Egg yolk anti-parasite antibodies can be raised in the hens of any avian species; however, use of hens of the common chicken, which are available in abundant commercial supply, and are adapted to egg production, are preferred. The hens can be immunized intramuscularly, intraperitoneally, or by other routes, according to methods and immunization schedules known to those in the art, for example, as described in Example 1, or as described by Losch, U., *J. Veterinary Medicine* 33:609–619 (1986). The co-administration of an adjuvant, such as Freund's (FCA; Sigma, St. Louis, Mo., Cat. No. F5881, 4258) increases and maintains the antibody level in the blood serum of the immunized animal. An enhanced responsiveness to the *Cryptosporidium* antigens used to immunize hens according to the method of the invention can be produced by substituting *Mycobacterium avium* for *M. tuberculosis* (1 mg/ml) in the Freund's adjuvant preparation. The use of *M. avium* also produce egg yolk antibodies to this endemic avian bacteria in the egg yolk product. The anti-parasite antibody thus induced is collected by harvesting the yolks of the eggs layed by the hyperimmune hens. Antibody-containing yolk fractions, or purified anti-parasite antibodies can be prepared as necessary.

The titer of the antibody thus raised can be determined by common immunological methods, for example, by an ELISA procedure as described in Example 1, or by Leslie, G. et al., *J. Exp. Medicine* 130:1337–1352 (1969), or by Ouchterlony or rocket immunoelectrophoresis, and can be quantitated against a known antigen preparation, either relatively or absolutely.

Antibody can be raised to a specific parasite by injecting an immunizing antigenic preparation derived from the entire parasitic structure, or antigenic portions thereof. For example, in preparing antibodies against *C. parvum*, proteinaceous extracts of the oocysts, sporozoites, merozoites, or antigens from any of the sexual stages of the parasite can be injected into the hen fowl. All isotypes of antibody raised in the hen are transferred from the hen serum into the developing egg yolk and through the oviduct to the developing egg white, and antibody level in the eggs produced peaks in about one week following a serum peak level.

Whole chicken serum contains antibodies of classes of about 31S, 16.1S, 7.3S, and 4.0S. The 7S class, is different in size from human IgG, against which it is frequently measured. It is also markedly resistant to temperature and acidity, an important feature in the commercial advantages of this type of immunity conferring agent. Antibody of any of these avian classes can be used in the methods of the invention; however, the use of an immunoglobulin fraction comprising the low molecular weight species of about 7S class is preferred as a purified antibody for the passive immunizations according to the invention.

Preparations of HEY Anti-Parasite Antibodies

The immunity-conferring egg yolk antibodies of the produced by the immunization of hens as described above can be used therapeutically or prophylactically in the form of unpurified native whole egg yolk, or in fractionated or purified preparations isolated from the yolk, provided the native, fractionated, or purified product contains an immunity-conferring amount of HEY anti-parasite antibodies.

Antibody-containing egg yolk fractions can be prepared by various methods known for separating proteinaceous material from natural sources, such as, for example, differential centrifugation, as described in Example 2, salt fractionation with ammonium sulfate or alcohol, or polyethylene glycol precipitation of proteins. A protein fraction enriched in antibodies can be obtained by solvent extraction of yolk lipids. Preparations of this type are described in U.S. Pat. Nos. 4,357,272 and 4,550,019 to Polson. Whole egg yolks or crude fractions thereof can be prepared by spray-drying, freeze-drying to form powdered preparations.

Hyperimmune whole egg yolks and crude egg yolk fractions containing anti-parasite antibodies are effective to confer immunity even when partially cooked by heating to the consistency of soft boiled egg yolk. They can more precisely be prepared by heating to a temperature of about 200° F., preferably at the boiling point of water, for a period of from about one to three minutes. The procedure can be carried out conveniently by placing the intact egg in boiling water for this period of time. The heating procedure can be carried out to "pasteurize" the eggs to eliminate any infectious organisms or to provide a more palatable preparation for oral ingestion. Pasteurization is described in standard texts on food processing, and typically comprises heating the eggs or fractions thereof to about 145°–150° F. for about 30 min, lowering the temperature to about 138° F. for several minutes, followed by cooling to about 50° F. Hyperimmune egg yolks of fractions thereof can be stabilized against decomposition caused by changes in acidity or alkalinity by the use of buffering agents.

Highly purified hen egg yolk antibodies or antibodies of distinct classes can be obtained by means of conventional protein purification procedures known for the isolation of immunoglobulins; for example, gel filtration, ion-exchange chromatography, ion-exchange chromatography, affinity chromatography, or isoelectric focusing.

The anti-parasitic hen egg yolk antibodies of the invention can be also administered in a complex including an anti-parasitic drug, wherein the antibody targets that drug to the parasite. In a preferred complex, the anti-parasitic drug is an anti-helminthic agent, and the anti-helminthic antibody-drug complex is administered in the form of a targeted liposomal complex, in which the anti-helminthic agent is encapsulated in a liposome as described, for example, by Alving, C. R., et al. *Proc. Natl. Acad. Sci.USA* 75(6):2959–2963 (1978), and the liposomal formulation includes anti-helminthic antibodies. Immunoliposomes formed by incorporating antibodies into liposomes to create immunoliposomes have been described by Huang, A. et al., *J. Biol. Chem.* 255:8015–8018 (1980), and Leserman, L. et al., *Nature* 288:602 (1980). According to the invention, the antihelminthic agent is released when the antibody incorporated into the liposome binds to the parasite.

Candidates for Passive Immunization Therapy

The passive immunization methods of the invention can be beneficially applied to either prevent infection by parasitic organism to an individual at risk for such infection, or to eliminate parasites from an infected individual. The recipient can be of any age, either newborn, a developing child, or an adult. The effectiveness of the passive immunization methods are independent of the immune status of the recipient, that is, immunocompetent, immunocompromised, or immunotolerant. In a preferred embodiment, the recipient is infected with a protozoan parasite, *C. parvum*.

Enteral Administration of HEY Antibodies

The dosage of passively immunizing antibodies for a vertebrate to be treated, including a human, may vary depending upon the extent and severity of the condition that is treated and the titer of the administered immunoglobulin fraction. Thus the dose of egg yolk product administered per day can range from about 0.1 mg/kg to about 1000 mg/kg. The egg yolk fraction as described in Example 4 can be administered to a 70 kg human at a preferred dose of about 100 to 200 mg/hr over a 24 hour period to provide a total daily dose of about 2400 to 4800 mg or about 33 to 66 mg/kg.

The prophylactic concentration of maternal antibodies found in bovine colostrum and human milk provides some guidance as to the optimal effective dose. The dosage of the hen egg yolk antibody fraction is determined by reference to these factors, bearing in mind that, in selecting the appropriate dosage in any specific case, consideration must be given to the patient's weight, general health, metabolism, age and other factors which influence response to the immunizing agent.

The prophylactic or therapeutic unit dose of hen egg yolk anti-parasitic antibodies can be administered by introduction into the digestive tract at any point and by any means so as to most effectively target the antibodies to the site of infection, for example, the intestinal villi. Enteral administration of a unit dose of antibody of this type has been carried out by coating the mouth (buccal swab), by encouraging voluntary ingestion by the recipient, through delivery by gastric intubation, by injection directly into a selected site in the intestinal tract, or by intubation into the intestine through the anus. Oral administration is preferred.

Formulations for oral ingestion are in the form of tablets, capsules, pills, ampoules of powdered antibody preparation, or oily or aqueous suspensions or solutions. Oral pharmaceutical formulations that are specific for immune globulins are disclosed in U.S. Pat. No. 4,477,432 to Hardie. Tablets or other non-liquid oral compositions may contain acceptable excipients, vehicles, diluents, fragrances, or flavors known to the art for the manufacture of pharmaceutical compositions, to make the medication palatable or pleasing to use. The formulation can therefore include diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract.

Aqueous suspensions may contain the active ingredient in admixture with pharmacologically acceptable excipients, comprising suspending agents, such as methyl cellulose; and wetting agents, such as lecithin or long-chain fatty alcohols. The aqueous suspensions may also contain preservatives, coloring agents, flavoring agents and sweetening agents in accordance with industry standards. The preparations may further comprise antioxidants, such as ascorbic acid or tocopherol, and preservatives, such as p-hydroxybenzoic acid esters.

Formulations comprising hyperimmune egg fractions or antibodies isolated therefrom can also contain other therapeutically active agents; for example, anti-diarrheal medications, anti-spasmodics, anti-helminthic agents, or antacids.

The present invention is described below in detail using the following examples, but the procedures described are disclosed in terms of their general application to the preparation of the hen egg yolk antibodies of the invention. Occasionally, the procedure may not be applicable as described to each immune preparation included within the disclosed scope of the invention. The preparations for which this occurs will be readily recognized by those skilled in the art. In all such cases, either the procedures can be successfully performed by conventional modifications known to those skilled in the art, e.g., by changing to alternative conventional reagents, or by routine modification of procedural conditions. Alternatively, other procedures disclosed herein or otherwise conventional will be applicable to the preparation of the corresponding preparations of the invention. In all preparative methods, all starting materials are known or readily prepared from known starting materials; all temperatures are set forth uncorrected in degrees Celsius; and, unless otherwise indicated, all parts and percentages are by weight.

It is believed that one skilled in the art can, using the preceding description, utilize the invention to its fullest extent. The following preferred embodiments are, therefore, to be construed as merely illustrative and not limitative for the remainder of the disclosure in any way whatsoever.

EXAMPLE 1

Immunization of Hens for Antibodies to *C. parvum*
Animals and Immunization Procedure Ten leghorn hens, 21 weeks old, were immunized subcutaneously according to the following protocols:

Group 1 received 25 µg of sonicated *C. parvum* oocysts emulsified in Freund's complete adjuvant (FCA);

Group 2 received 2.5 µg of the immunogen diluted in phosphate buffered saline, 0.025M, pH 7.4 (PBS).

Group 3 received FCA alone; and 3 additional hens were kept as controls.

Booster doses for all the groups were administered 5 weeks later; in this immunization FCA was replaced by Freund's incomplete adjuvant where applicable.

Egg and Blood Collection

Eggs were collected weekly and stored at 4° C. until processed. Blood samples were collected from the wing vein every other week, centrifuged at 200 g within 24 hours and sera stored at −200° C. until evaluated.

In Vitro Analysis

Yolks were mechanically separated from whites, placed on soft paper towels, and rolled until the yolk sacks were dried. The yolk sacks were torn with a plastic tip and the contents carefully poured into sterile 50-ml tubes and diluted 1:1 with sterile PBS. These yolk preparations were stored at −200° C. until analyzed by an enzyme-linked immunosorbent assay (ELISA).

To make hyperimmune yolk preparations (HYP), yolk contents were collected, diluted 1:1 with PBS, and centrifuged at 1,800 g for 15 min. Three different layers were differentiated: a yellowish clear top layer (fat), an intermediate liquid phase which contained IgY and other serum proteins, and a yellow pellet (casein-like proteins, vitellin). The fat was carefully removed and the second layer was collected and stored at −20° C. until used in the study.

EXAMPLE 2

Determination of Antibody Titer

ELISA: Ninety six well (flat bottom) plates (Nunc Immuno II) were coated with *Cryptosporidium parvum*-sonicated antigen (10 µg/ml) in carbonate buffer, pH 9.6. Plates were incubated overnight at 4° C. and blocked with 200 µl per well using 1% Hammersten casein at 37° C. for one hour. One hundred microliters per well of diluted samples (1:1000) were added in triplicate, incubated at 37° C. for one hour, and 100 µl per well of goat anti-chicken IgG (IgY) conjugated with horseradish peroxidase (Kirkegard and Perry Laboratories; 1:1000 dilution) was added. After 1 hour incubation, the substrate (TMB, Kirkegard and Perry Laboratories) was added according to the manufacturer's instructions and the reaction was stopped 3 min later with 0.1 M phosphoric acid. Optical densities of the wells were determined in a dynatech ELISA reader at 450 nm and the information was stored in database files for further analysis.

The ELISA activities showed a marked increase in the anti-*C. parvum* activities from animals in Group 1, peaking by 5 week post-immunization and maintaining those high activities for at least the next 17 weeks. Groups 2 and 3 also had an increase in their anti-*C. parvum* activities, with higher levels in Group 2, but significantly lower than in Group 1. In Group 3 (control) no significant changes were detected. Anti-*C. parvum* activities in the egg yolk preparations followed a pattern similar to that described for the blood samples with very similar OD values (FIG. 1). The anti-*C. parvum* IgY activities were maintained at high levels as a results of the immunization schedule utilized in this study.

EXAMPLE 3

Passive Immunization of Neonatal Mice Against *C. parvum* and Challenge

Animals: Term pregnant BALB/c mothers were purchased from Harlan Sprague-Dawley (Indianapolis, Ind.). Within 24 hours of delivery (day-1) all mice (adults and neonates) were randomized and 7 neonates were distributed with each mother. This procedure was performed in order to minimize biological differences between litters. At day 6, the neonatal mice were orally infected with $5 \times 10^5$ *C. parvum* oocysts by gastric gavage using polyethylene tubing (1.09 mm O.D., Intramedic, Becton Dickinson) and 27-gauge needles. Mice were treated on days 8 to 12, receiving 100 µl of their respective products (HYP or PBS) administered by gastric gavage as previously described. Four treatment groups were established: Groups A, B and C received HYP from hens in Groups 1, 2 and 3 respectively; and Group D which received sterile PBS only. On day 13, the experimental animals were euthanized by cervical dislocation. The terminal ilium was collected, placed in 10% formalin, and processed for routine histopathologic processing. Sections were stained with hematoxylin and eosin and examined using a bright field microscope. Two high power fields (X400) were examined per mouse. The presence of parasites was quantified in all cross and longitudinal sectors of villi observed within the field. The mean parasite load per villus was determined for each animal and the results were analyzed by 1-way analysis of variance (ANOVA).

The overall rates of mortality and infectivity in this study were 1.25% and 100% respectively, indicating that neither the randomization procedure nor the gastric gavage had significant influences on the results. Parasite quantitation from histological sections from the four groups was summarized in Table 1. Administration of HYP from group 1 (*C. parvum*+FCA) to group A resulted in a significant reduction in the degree of parasitism (P<0.001) when compared to all the other groups. Group B showed a significant parasite reduction when compared to the controls (P<0.05). These results strongly suggest that reductions in *C. parvum* loads in the experimental animals were associated with significantly increased activities in the anti-*C.parvum* IgY in the HYP.

| Treatment | Receiving Yolks | | | Control |
|---|---|---|---|---|
| Group | A | B | C | D |
| Product Administered | HYP from Group 1 | HYP from Group 2 | HYP from Group 3 | PBS |
| Parasite/Villus | 4.55 | 14.25 | 22.30 | 29.74 |

It should be apparent from the foregoing that other avian animals or antibody preparations can be substituted in the Examples to obtain similar results of passively immunizing a vertebrate animal effectively through the oral route. It should be further emphasized that the present invention is not limited to the use of any particular antigenic agent in producing the antibody preparations of the invention. Thus, regardless of whether a specific parasitic agent or its antigen is presently known, or whether it becomes known in the future, the methods of forming the presently contemplated HEY antibody preparations therefrom are based on established chemical techniques, as will be apparent to those of skill in the art, and therefore these preparations are broadly enabled by the preceding disclosure. It should be emphasized again that the present methods are broadly applicable to formation of antibody preparations from essentially all parasitic antigens, and the immunization of a vertebrate to these parasites be improved by preparing an avian antibody oral form for use in the practice of the invention.

Accordingly, the invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within their scope.

What is claimed is:

1. A method of treating an intestinal parasitosis caused by *Cryptosporidium parvum* in a mammal in need thereof, comprising the enteral administration to said mammal of an effective parasite-reducing amount of hen egg yolk antibodies having a specificity for at least one antigen of *Cryptosporidium parvum*.

2. A method according to claim 1 wherein said hen egg yolk antibodies are administered as a preparation comprising the yolks of eggs from hyperimmunized hens.

3. A method according to claim 1, wherein said enteral administration comprises oral ingestion, gastric intubation, rectal intubation, or direct injection of said hen egg yolk antibodies into the intestinal tract of said mammal.

4. A method according to claim 1 wherein said hen egg yolk antibodies have a specificity for at least one antigen of the oocyst, sporozoite, merozoite, or any sexual stage of said *Cryptosporidium parvum*.

5. A method according to claim 1 wherein the intestinal parasitosis is an opportunistic infection in a mammal that is immunologically compromised.

6. A method according to claim 5 wherein said mammal is a human who is infected with human immunodeficiency virus.

7. A method according to any one of claims 1–4 or 5 wherein said mammal is a human being.

* * * * *

UNITED STATES PATENT AND TRADEMARK OFFICE
CERTIFICATE OF CORRECTION

PATENT NO. : 5,753,228
DATED : May 19, 1998
INVENTOR(S) : Sterling, Charles R., et al.

It is certified that error appears in the above-identified patent and that said Letters Patent is hereby corrected as shown below:

At Column 8, Line 39, Delete "-200°C" and substitute ---20°C---
At Column 8, Line 46, Delete "-200°C" and substitute ---20°C---

Signed and Sealed this

First Day of September, 1998

*Attest:*

*Attesting Officer*

BRUCE LEHMAN

*Commissioner of Patents and Trademarks*